(12) United States Patent
Miles et al.

(10) Patent No.: US 6,686,496 B1
(45) Date of Patent: Feb. 3, 2004

(54) TREATMENT OF MYELOMA

(75) Inventors: D. Howard Miles, Winter Springs, FL (US); Solodnikov Sergey Yurjevich, Perm (RU); Krasnykh Olga Petrovna, Perm (RU); Korotkova Tatiana Alexandrovna, Orlando, FL (US); Elena A. Goun, Stanford, CA (US)

(73) Assignee: University of Central Florida, Orlando, FL (US)

( * ) Notice: Subject to any disclaimer, the term of this patent is extended or adjusted under 35 U.S.C. 154(b) by 47 days.

(21) Appl. No.: 10/165,027

(22) Filed: Jun. 7, 2002

Related U.S. Application Data

(60) Provisional application No. 60/296,823, filed on Jun. 8, 2001.

(51) Int. Cl.$^7$ ............................................. C07C 205/00
(52) U.S. Cl. ............................... 560/22; 560/5; 560/19; 560/20; 560/21; 560/22
(58) Field of Search ................................. 560/5, 19, 20, 560/21, 22; 562/459; 514/524, 557

(56) References Cited

U.S. PATENT DOCUMENTS

| | | | | |
|---|---|---|---|---|
| 3,862,954 | A | 1/1975 | Omodei-Sale | 260/296 |
| 5,274,002 | A | 12/1993 | Hawkins | 514/530 |
| 5,308,852 | A | 5/1994 | Girard | 514/336 |
| 5,334,612 | A | 8/1994 | Kalden | 514/440 |
| 6,048,896 | A | 4/2000 | Giordani | 514/545 |
| 6,066,670 | A | 5/2000 | Brown | 514/557 |
| 6,080,790 | A | 6/2000 | Boyd et al. | 514/650 |
| 6,121,450 | A | 9/2000 | Jones | 546/81 |
| 6,180,651 | B1 | 1/2001 | Nicolai | 514/336 |
| 6,232,312 | B1 | 5/2001 | Pamukcu | 514/237.5 |
| 6,602,907 | B1 * | 8/2003 | Miles et al. | 514/523 |

* cited by examiner

*Primary Examiner*—Johann Richter
*Assistant Examiner*—Karl Puttlitz
(74) *Attorney, Agent, or Firm*—Brian S. Steinberger; Roland Dexter; Law Offices of Brian S. Steinberger, P.A.

(57) ABSTRACT

The compounds of the invention which encompasses a class of compounds having the property of anti-carcinogenic activity against human myeloma r comprising 4-oxo-2-butenoic acid compounds and 3-hydrazino-2,4-dioxobutanoic acid compounds and more specifically those novel derivatives: 4-(4-Chloro-phenyl)-2-(N'-fluoren-9-ylidene-hydrazino)-4-oxo-but-2-enoic acid methyl ester (OF-07); 2-{N'-[(2-Bromo-phenyl)-phenyl-methylene]-hydrazino}-4-oxo-4-phenyl-but-2-enoic acid methyl ester (OF-09); 2-{N'-[(4-Dimethylamino-phenyl)-phenyl-methylene]-hydrazino}-4-oxo-4-phenyl-but-2-enoic acid methyl ester (OF-10) and 2-{N'-[1-(4-Chloro-phenyl)-ethylidene]-hydrazino}-4-oxo-4-phenyl-but-2-enoic acid methyl ester (OF-20) and the use of 2-(N'-Fluoren-9-ylidene-hydrazino)-5,5-dimethyl-4-oxo-hex-2-enoic acid methyl ester (OF-06); 4-(4-Ethoxy-phenyl)-2-(N'-fluoren-9-ylidene-hydrazino)-2-hydroxy-4-oxo-butyric acid methyl ester (OF-13); 4-benzoyl-3 -benzoyloxy-2-(2-oxo-2H-1,4-benzoxazin-3-yl)pyrido[2,1-c][1,4]benzoxazin-1,5-dione (1F-18), 4-Chloro-4-(4-ethoxy-phenyl)-2-(fluoren-9-ylidene-hydrazono)-but-3-enoic acid methyl ester (3F-19); and 2-(N'-Fluoren-9-ylidene-hydrazino)-4-oxo-4-phenyl-but-2-enoic acid methyl ester (1F-04) which are unique in humans as therapeutic means for the eradication human myeloma.

2 Claims, 1 Drawing Sheet

TREATMENT OF MYELOMA

This invention claims the benefit of priority of U.S. Provisional Application Serial No. 60/296,823 filed Jun. 8, 2001.

FIELD OF THE INVENTION

This invention relates to compounds that are 4-oxo-2 butenoic acid and 3-hydrazino-2,4-dioxobutanoic acid derivatives and more particularly to the use of these derivatives for treatment of human myeloma.

BACKGROUND OF THE INVENTION

Cancer is a global killer of humans with breast cancer and colon cancer among the leaders with many other types killing modest amounts of humans yearly including human myeloma for which there appears to be no cure.

Myeloma is a cancer of plasma cells. Plasma cells are normally present in the bone marrow and are responsible for antibody production in response to infection and other immune triggering events. In myeloma, a single defective plasma cell (myeloma cell) gives rise to the much larger number of myeloma cells which build up in the bone marrow. This process disrupts the normal immune system as well as displacing the normal bone marrow cells. The myeloma cells divide and grow more frequently than normal plasma cells and develop cancerous properties which enable myeloma cells to invade and damage bone as well as travel through the blood stream to other bone marrow sites. Because there is no known cure, treatments need to be viewed in terms of how long they are able to control the disease or relieve symptoms and how they affect the patient's quality of life.

There are over 13,500 new cases of myeloma in the U.S. each year representing 20% of blood cancers and 1% of all types of cancer. The incidence varies from country to country from a low 1/100,000 in China to approximately 4/100,000 in most Western industrialized countries.

The U.S. patent literature has many disclosures of oxo-butenoic (crotonic) compounds:

Pamukci (U.S. Pat. No. 6,232,312) describes crotonic acid derivatives (column 22, lines 43–58) for the treatment of colonic polyps;

Jones et al (U.S. Pat. No. 6,121,450) discloses crotonic acid derivatives (column 8, tine 34; column 78, line 24 and at example 34 as steroid modifiers in treating breast cancer (column 1, lines 55–58);

Kalden, et al (U.S. Pat. No. 5,334,612) discloses compounds said to be useful for treating AIDS including derivatives of carboxylic acid (column 9, line 31) and pyrrolidine (column 7, line 24);

Brown (U.S. Pat. No. 6,066,670) describes an anti-viral admixture containing crotonic acid for treating tumors (see Abstract);

Horwell, et al (U.S. Pat. No. 5,580,896) discloses many 4-oxo-2-butenoic acid derivatives (column 13, lines 21–59; also in columns 15+, examples acid derivatives (column 13, lines 21–59; also in columns 15+, examples 25,26,32,34,40,43–46,77–79,97,99,103, 106,), which are useful for inhibiting colorectal cancer, i.e., colon cancer (Abstract);

Giordani, et al (U.S. Pat. No. 5,580,890) discloses 4-oxo-2-butenoic acid derivatives said to be useful for treatment of AIDS (column 1, line 8 and column 2, line 61; and, Yonemeto, et al (U.S. Pat. No. 6,083,985) recites a number of anti-tumor or anti-AIDS agents that include heterocylic butenoic acid derivatives.

The U.S. patent literature has many disclosures of butanoic acid derivatives including:

Nicolai, et al (U.S. Pat. No. 6,180,651) discloses many anti-inflammatory and analgesic compounds, including adenocarcinoma (column 1, line 55), which includes heterocyyclic alcohol-esters (column 11, lines 1–16) and butanoic acid derivatives (many Examples including 47 through 162);

Girard, et al (U.S. Pat. No. 5,308,852) discloses many compounds including butanoic acid derivatives (see Methods B and C of schemes II and III) which compounds which are said to inhibit tumor metastasis (column 7, line 56 and column 8, line 4);

Frechette (U.S. Pat. No. 5,696,117), Frechette(5,854,242) and Frechette (U.S. Pat. No. 5,707,990) describe 148 benzoxazine and pyrido-oxazine heterocyclic as antibacterial compounds;

Omedi-Sale (U.S. Pat. No. 3,862,954) shows tri-azole compounds for CNS use;

Hawkins (U.S. Pat. No. 5,274,002) describes many analogs of phenyl ethers of a substituted phenyl of the formula structure at column 1, lines 49–60 with 37 examples of specific compounds which compounds may be useful for tumor inhibition (column 22, line 64); and, Boyd, et al (U.S. Pat. No. 6,080,790) also describes many tri-substituted phenyl derivatives according to the formula of the Abstract with 15 examples of specific compounds which may be useful for malignant skin diseases (column 5, line 46).

It appears from a review of the foregoing that the oxo-butenoic derivatives of interest are not disclosed and thus there is no report of their activity against human myeloma.

Consequently, there is a need for an anti-cancer drug for humans that mitigates the above mentioned disadvantages of current drug therapy and effectiveness against human myeloma.

SUMMARY OF THE INVENTION

The objective of the present invention is to provide a drug effective for treatment of human myeloma.

Preferred embodiments of the invention encompass novel compounds of derivatives of 4-oxo-2-butenoic acid comprising the property of anti-tumor activity against human myeloma and more specifically those novel compounds, alone or in admixture: OF-07; OF-09; OF-10; and OF-20 and the use of the compounds: OF-06, OF-07; OF-09; OF-10; OF-13; OF-20; IF-04; IF-18 and, 3F-19 in humans as therapeutic means for the eradication of the myeloma carcinogens from the human's body.

Further objects and advantages of this invention will be apparent from the following detailed description of presently preferred embodiments which are illustrated structurally in the accompanying drawings.

DESCRIPTION OF THE PREFERRED EMBODIMENTS

Figure 1:
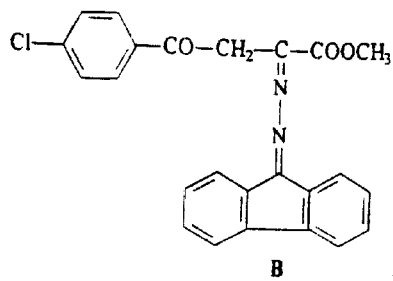
FIG. 1 illustrates structurally a chemical compound designated as OF-07.
Figure 2:
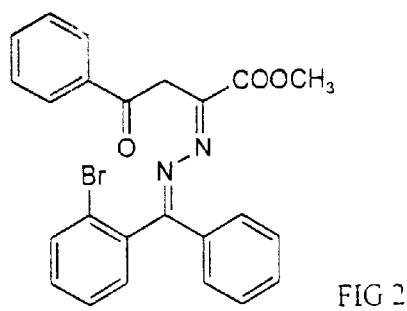
FIG. 2 illustrates structurally a chemical compound designated as OF-09.
Figure 3:
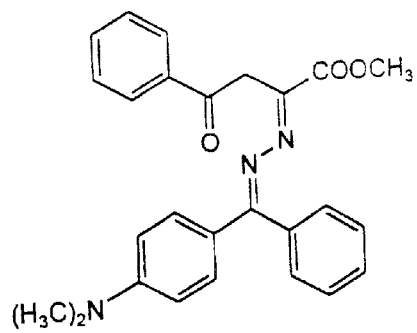
FIG. 3 illustrates structurally a chemical compound designated as OF-10.
Figure 4:
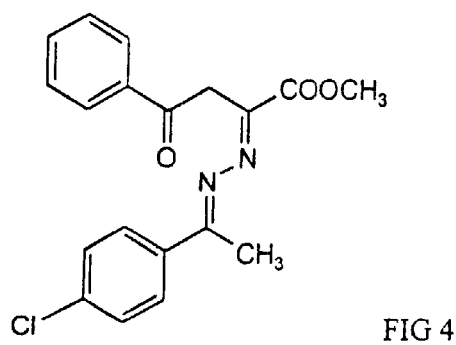
FIG. 4 illustrates structurally a chemical compound designated as OF-20.

Before explaining the disclosed embodiments of the present invention in detail, it is to be understood that the invention is not limited in its application to the details of the particular arrangement shown since the invention is capable of other embodiments. Also, the terminology used herein is for the purpose of description and not of limitation.

As earlier recited this application has been filed in order to both disclose: the novel derivatives of and the specified derivatives of 4-oxo-2-butenoic acid and the 3-hydrazino-2,4-dioxobutanoic acid that are useful for the in vitro treatment of human beings inflicterd with myeloma.

To facilitate a full understanding of the invention:

the compound designated as OF-07 4-(4-Chloro-phenyl)-2-(N'-fluoren-9-ylidene-hydrazino)-4-oxo-but-2-enoic acid methyl ester;

the compound designated as OF-09 is 2-{N'-[(2-Bromo-phenyl)-phenyl-methylene]-hydrazino}-4-oxo-4-phenyl-but-2-enoic acid methyl ester;

the compound designated as OF-10 is 2-{N'-[(4-Dimethylamino-phenyl)-phenyl-methylene]-hydrazino}-4-oxo-4-phenyl-but-2-enoic acid methyl ester; and, the compound designated as OF-20 is 2-{N'-[1-(4-Chloro-phenyl)-ethylidene]-hydrazino}-4-oxo-4-phenyl-but-2-enoic acid methyl ester.

As well as the compounds recited above, those found to have use for the treating of human myeloma also include:

2-(N'-Fluoren-9-ylidene-hydrazino)-5,5-dimethyl-4-oxo-hex-2-enoic acid methyl ester (OF-06); 4-(4-Ethoxy-phenyl)-2-(N'-fluoren-9-ylidene-hydrazono)-but-3-enoic acid methyl ester (3F-19); and 2-(N'-Fluoren-9-ylidene-hydrazino)-4-oxo-4-phenyl-but-2-enoic acid methyl ester (1F-04).

These compounds have very high activity against myeloma and a very low toxicity as Lethal Dose 50 ($LD_{50}$) in animals. The percent activity and animal toxicity for each compound is as follows: OF-06 (82% against human myeloma and $LD_{50}$>3000 mg/kg); OF-07 (74% against human myeloma and $LD_{50}$>750 mg/kg); OF-09 (86% against human myeloma and $LD_{50}$>5000 mg/kg); OF-10 (96% against human myeloma and $LD_{50}$>1500 mg/kg); OF-13 (99% against human myeloma and $LD_{50}$>1500 mg/kg); 0F-20 (84% against human myeloma and $LD_{50}$>250 mg/kg); 1F-04 (77% against human myeloma and $LD_{50}$>1000 mg/kg) and 1F-18 (100% against human myeloma, and $LD_{50}$>2000 mg/kg); and 3F-19 (100% against human myeloma and $LD_{50}$>200 mg/kg).

PREPARATION OF (OF-07)

EXAMPLE 1

The preparation of 4-(4-Chloro-phenyl)-2-(N'-fluoren-9-ylidene-hydrazino)-4-oxo-but-2-enoic acid methyl ester (OF-07). A solution of 5.0 g (0.0208 moles) 4-(4-chloro-phenyl)-2-hydroxy-4-oxo-but-2-enoic acid methyl ester (1) and 3.88 g (0.02 moles) of fluoren-9-ylidene-hydrazine (2) in 50 mL of absolute toluene was refluxed for 2 hr with a Dean-Stark trap (the end of the reaction was determined by TLC). The resulting mixture was cooled, precipitate was filtered and recrystallized from benzene-heptene mixture (1:5) to give 5.80 g (67% yield) of orange-brown crystals with mp 167–168° C.

Solubility: highly soluble in DMSO, DMFA, dichloroethane, acetonitrile, insoluble in water.

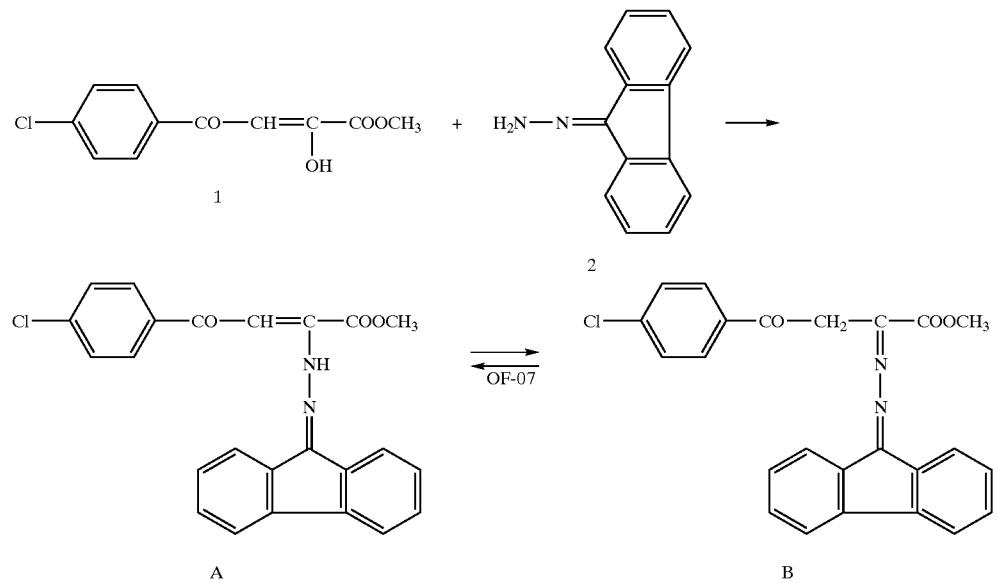

phenyl)-2-(N'-fluoren-9-ylidene-hydrazino)-2-hydroxy-4-oxo-butyric acid methyl ester (OF-13); 4-benzoyl-3-benzoyloxy-2-(2-oxo-2H-1,4-benzoxazin-3-yl)pyrido[2,1-c][1,4]benzoxazin-1,5-dione (1F-18), 4-Chloro-4-(4-ethoxy-phenyl)-2-

PREPARATION OF (0F-09)

EXAMPLE 2

The preparation of 2-{N'-[(2-Bromo-phenyl)-phenyl-methylene]-hydrazino}-4-oxo-4-phenyl-but-2-enoic acid methyl ester (OF-09). A solution of 6.0 g (0.0291 moles) of 2-hydroxy-4-oxo-4-phenyl-but-2-enoic acid methyl ester (1) and 5.71 g (0.0291 moles) of [(2-Bromo-phenyl)-phenyl-methylene]-hydrazine (2) in 80 mL of absolute toluene (1:1) was refluxed with a Dean-Stark trap (the end of the reaction was determined by TLC), cooled and the precipitate was filtered and recrystallized from benzene to give 10.24 g (76% yield) of colorless crystals with mp 119–120° C.

Solubility: highly soluble in DMSO, DMFA, dichloroethane, acetonitrile, insoluble in water.

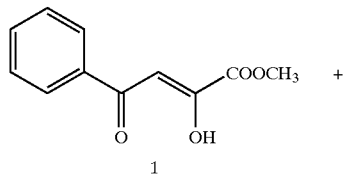

1

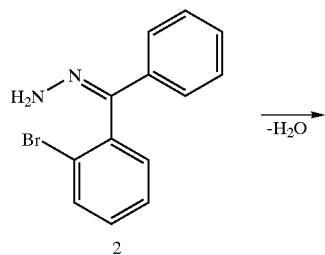

2

$-H_2O \rightarrow$

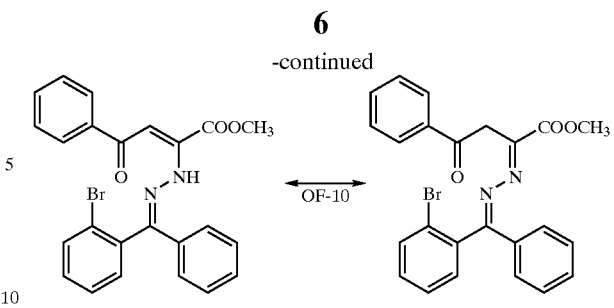

PREPARATION OF (OF-10)

EXAMPLE 3

The preparation of 2-{N'-[(4-Dimethylamino-phenyl)-phenyl-methylene]-hydrazino}-4-oxo-4-phenyl-but-2-enoic acid methyl ester (OF-10). A solution of 1.0 g (0.0048 moles) of 2-hydroxy-4-oxo-4-phenyl-but-2-enoic acid methyl ester (1) and 1.16 g (0.0048 moles) of [3-(Hydrazono-phenyl-methyl)-phenyl]-dimethyl-amine (2) in 30 mL of absolute benzene was refluxed with a Dean-Stark trap (the end of the reaction was determined by TLC), cooled and the precipitate was filtered and recrystallized from benzene-hexane mixture (4:1) to give 1.18 g (61% yield) of yellow crystals with mp 159–160° C.

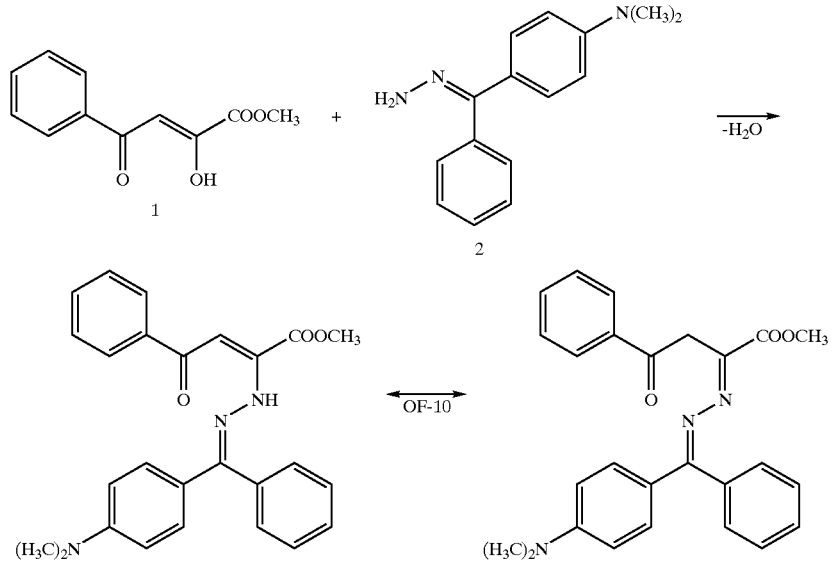

Solubility: highly soluble in DMSO, DMFA, dichloroethane, acetonitrile, chloroform, insoluble in water.

PREPARATION OF (OF-20)

EXAMPLE 4

The preparation of 2-{N'-[1-(4-Chloro-phenyl)-ethylidene]-hydrazino}-4-oxo-4-phenyl-but-2-enoic acid methyl ester (OF-20). A solution of 6.0 g (0.0291 moles) of methyl phenyl-2-hydroxy-4-oxo-4-phenyl-2-butenoate (1) and 4.91 g (0.0291 moles) of [1-(4-Chloro-phenyl)- ethylidene]-hydrazine (2) in 50 mL of absolute benzene) was refluxed for 15 min with a Dean-Stark trap (the end of the reaction was determined by TLC) and cooled. The resulting precipitate was filtered and recrystallized from benzene-hexane mixture (5:1) to give 4.36 g (42% yield) of yellow crystals with mp of 116–117° C. (decomp).

Solubility: highly soluble in DMSO, DMFA, dichloroethane, acetonitrile, chloroform, insoluble in water.

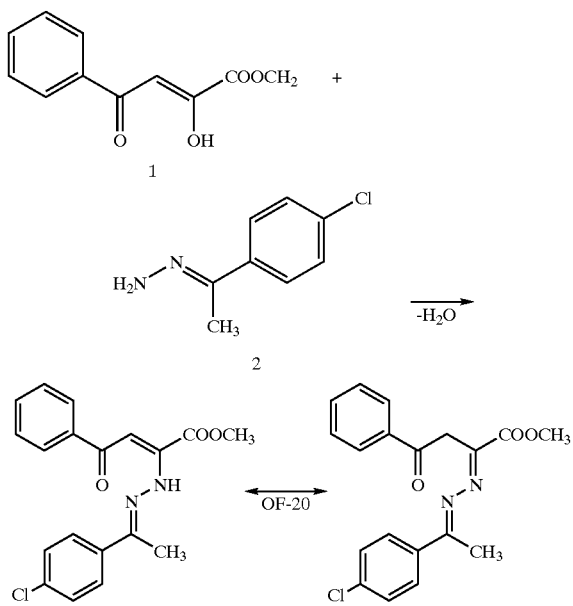

PREPARATION OF (OF-06).

EXAMPLE 5

The preparation of 2-(N'-Fluoren-9-ylidene-hydrazino)-5,5-dimethyl-4-oxo-hex-2-enoic acid methyl ester (OF-06). A solution of 5.0 g (0.02 moles) of 2-hydroxy-5,5-dimethyl-4-oxo-hex-2-enoic acid methyl ester (1) (synthesis was previously published by E. Royals. *J.Am.Chem.Soc.*, 1945, 67, 1508) and 3.88 g (0.02 moles) of fluoren-9-ylidene-hydrazine (2) in 80 mL of absolute toluene was refluxed for 3 hr 30 min with a Dean-Stark trap (control for the end of the reaction was carried by TLC). The solution was cooled and the precipitate was filtered and recrystallized from absolute benzene-hexane (1:1) to give 3.4 g (68% yield) of yellow crystals, mp 135–137° C.

Solubility : highly soluble in DMSO, DMFA, dichloroethane, acetonitrile, slightly soluble in ethanol, tetrachloromethane, insoluble in hexane and water.

The synthesis of 0F-06 is an example of well known amination/dehydration reactions.

PREPARATION OF (OF-13)

EXAMPLE 6

The preparation of 4-(4-Ethoxyphenyl)-2-(N'-fluoren-9-ylidene-hydrazino)-2-hydroxy-4-oxobutyric acid methyl ester (OF-13). A solution of 5.0 g (0.02 moles) of methyl 4-p-ethoxyphenyl-2-hydroxy-4-oxo-2-butenoate (1) and 3.88 g (0.02 moles) of fluorene-9-ylidene-hydrazine (2) in 80 mL of absolute benzene and absolute toluene (1:1) was refluxed for 1 hr 30 min with a Dean-Stark trap (the end of the reaction was determined by TLC), cooled and the precipitate was filtered and recrystallized from benzene-diethyl ether-hexane mixture (1:3:2) to give 2.65 g (53% yield) of colorless crystals with mp 114–116° C.

Solubility: highly soluble in DMSO, DMFA, dichloroethane, acetonitrile, insoluble in hexane. The compound is not stable in solutions and decomposes quickly when the solution is heated or stored for a long time with the formation of OF-12.

PREPARATION OF (IF-18)

EXAMPLE 7

The preparation of 4-benzoyl-3-benzoyloxy-2-(2-oxo-2H-1,4-benzoxazin-3-yl)pyrido[2,1-c][1,4]benzoxazin-1,5-dione (IF-18).

A solution of 1.5 g (0.047 moles) of compound 4* in 10 mL of dowtherm A** was kept at constant temperature at 183–186° C. for 30 min. The solution was cooled and the resulting precipitate of 1F-18 was filtered and recrystallized from acetonitrile to give 0.79 g (54%) of orange crystals with mp of 259–261° C. (decomposed).

* A detailed synthesis of compound 4 has been published earlier in: Five-membered-ring 2,3-dioxoheterocycles. XXXIII. Synthesis of 3-aroyl-1,2-dihydro-4H-pyrrolo[5,1-c][1,4]benzoxazine-1,2,4-triones and their reaction with water and alcohols. Mashivets, A. N.; Mashevskaya, I. V.; Krasnykh, O. P.; Shurov, S. N.; Andreichikov, V. S. Perm. Gos. Univ., Perm, Russia. Zh. Org. Khim. (1992),
** Content: 73.5% phenyl ether 26.5% diphenyl Described in L.Fieser, M.Fieser, Reagents for Organic Synthesis, Wiley, New York, 1968.

PREPARATION OF (3F-19)

EXAMPLE 8

The preparation of 4-Chloro-4-(4-ethoxy-phenyl)-2-(fluoren-9-ylidene-hydrazono)-but-3-enoic acid methyl ester (3F-19) To the solution of 10 g (0.0026 moles) of 4-(4-Ethoxy-phenyl)-2-(N'-fluoren-9-ylidene-hydrazino)-4-oxo-but-2-enoic acid methyl ester (1) (synthesis was previously published by Miles et.al., UCF-311A) in 5 mL of anhydrous benzene 0.3935 g (0.0031 moles) oxalyl chloride was added. The reaction mixture was refluxed for 1 hour 40 min, cooled, the precipitate was filtered and recrystallized from absolute benzene to give 0.62 g (54%) of yellow crystals, m.p. 163–163 (decomp).

A synthesis of compound 3F-19 has been published earlier in: Konyukhova, N. A.; Kiasnykh, O. P.; Aliev, Z. G.; Maslivets, A. N. *Chemistry of Heterocyclic Compounds* (New York, N.Y., United States)(Translation of *Khimiya Geterotsiklicheskikh Soedinenii*) (2001), 37(6), 779–780)

PREPARATION OF (IF-04)

EXAMPLE 9

The preparation of 2-(N'-Fluoren-9-ylidene-hydrazino)-4-oxo-4-phenyl-but-2-enoic acid methyl ester (1F-04). A solution of 5.0 g (0.0242 moles) 4-phenyl-2-hydroxy-4-oxo-but-2-enoic acid methyl ester (1) and 4.70 g (0.0242 moles) of fluoren-9-ylidene-hydrazine (2) in 30 mL of toluene was refluxed for 2.5 hr with a Dean-Stark trap (the end of the reaction was determined by TLC). The resulting mixture was cooled, precipitate was filtered and recrystallized from hexane to give 5.83 g (63% yield) of orange-brown crystalls with mp 133–134° C.

Solubility: highly soluble in DMSO, DMFA, dichloroethane, acetonitrile, insoluble in water.

The synthesis of 0F-06 is an example of well known amination/dehydration reactions.
A synthesis of compound 1F-4 has been published earlier in: Andrejchikov, Yurij S.; Maslivets, Andrej N.; Krasnykh, Olga P.; Aleksandrova, Galina A.; Vozhakova, Alla V. Russ. (1993), CODEN: RUXXE7 RU 2003655 C1 19931130 Application: RU 91-5013322 19910704

TABLE 1

*Compounds claimed for use in treatment of myeloma only.*

| | Structure | Name | Activity (ATCC CCL155) | LD$_{50}$ mg/kg | Reference |
|---|---|---|---|---|---|
| OF-06 | 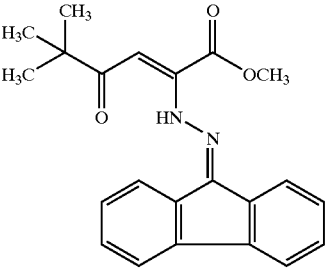 | 2-(N'-Fluoren-9-ylidene-hydrazino)-5,5-dimethyl-4-oxo-hex-2-enoic acid methyl ester | 82% | >3000 | Miles et. al., UCF-311A |
| OF-13 | 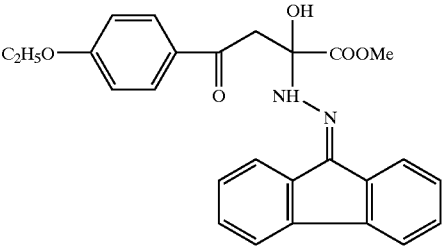 | 4-(4-Ethoxy-phenyl)-2-(N'-fluoren-9-ylidene-hydrazino)-2-hydroxy-4-oxo-butyric acid methyl ester | 99% | >1500 | Miles et. al., UCF-303A |
| IF-18 | 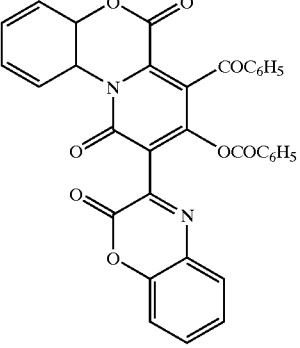 | Benzoic acid 1-benzoyl-4,10-dioxo-3-(2-oxo-2H-benzo[1,4]oxazin-3-yl)-4,4b,8a,10-tetrahydro-9-oxa-4a-aza-phenanthren-2-yl ester | 100% | >2000 | Miles et. al., UCF-303B |
| 3F-19 | 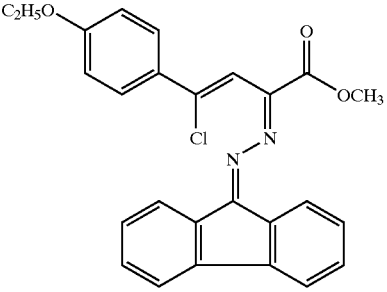 | 4-Chloro-4-(4-ethoxy-phenyl)-2-(fluoren-9-ylidene-hydrazono)-but-3-enoic acid methyl ester | 100% | >200 | Konyukhova, N. A.; Krasnykh, O. P.; Aliev, Z. G.; Maslivets, A. N. Chemistry of Heterocyclic Compounds (New York, NY, United States) (2001), 37(6), 779–780. |
| IF-04 | 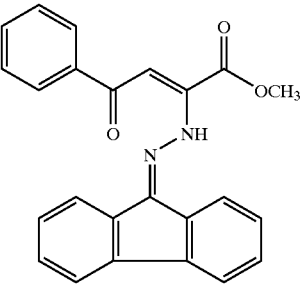 | 2-(N'-Fluoren-9-ylidene-hydrazino)-4-oxo-4-phenyl-but-2-enoic acid methyl ester | 93% | >1000 | Andrejchikov, Yurij S.; Maslivets, Andrej N.; Krasnykh, Olga P.; Aleksandrova, Galina A.; Vozhakova, Alla V. Russ. (1993), CODEN: RUXXE7 RU 2003655 C1 19931130 Application: RU 91-5013322 19910704. |

CYTOTOXICITY ASSAY

The anticancer activity against human myeloma of the novel compounds (as earlier reported) was realized by the following procedure which determines the inhibitory effect of test samples on the growth of human myeloma cells.

The anti-carcinogenic activity against human cancer of the novel compounds (as earlier reported) was realized by the following procedure which determines the inhibitory effect of test samples on the growth of human breast cancer cells.

(ATCC CCL155) The CCL155 cells are grown in RPMI 1640 media+20% Fetal bovine serum+4.5 g/L glucose+10 mM HEPES+1.0 mM sodium pyruvate+1% Antibiotic/Antimycotic for approximately 48 hours at 37° C./5% $CO_2$ in the presence of the test compound.

Growth/Non-Growth of the cells (e.g., cell density) is determined using Promega's MTS/PMS assay system. MTS (3-(4,5-dimethylthiazol-2-yl)-5-(3-carboxymethoxyphenyl)-2-(4-sulfophenyl)-2H-tetrazolium, inner salt) is an aqueous compound that is reduced to soluble formazan by the presence of NADH formed by dehydrogenases present within the CCL155 cells. The absorbance of the formazan can be measured at 490 nm and is directly proportional to the number of living cells present in the culture. PMS (Phenazine Methosulfate) is added an electron coupling reagent and greatly increases the rate of reduction.

To facilitate a full understanding of the procedure the following definitions are offered:

Test wells—wells containing test sample and Diluted CCL155 cells

Test values—absorbance of test wells

Blank wells—wells containing test sample and CCL155 media (C155-01S); used to obtain background absorbance due to test sample Blank values—absorbance of blank wells Negative Control—maximal cell growth; results of test samples will be expressed as a percent of the Negative Control Positive Control—known inhibitor of CCL155 cells; used to validate assay system Matrix—solvent that the samples are prepared/diluted in Assay samples of similar origin and matrix (e.g., methanol extraction, methylene chloride extraction, water soluble samples, etc.) together on the same plate in order to reduce the number of steps performed per plate.

Blank values will be determined for each sample to account for any color contribution due to the sample itself. These blank wells must contain the same amount of sample plus CCL155 media (no cells). After completion of MTS/PMS reaction blank values will be subtracted from the test value to obtain a net absorbance that will be used to calculate cell density.

All results are based upon a comparison to the Negative Control value of the plate. The Negative Control must contain the same amount of matrix (e.g., solvent) to offset any destructive effect the matrix may have on the growth of the CCL155 cells (allows for baseline values to be set).

For most samples, a CCL155 cell growth (initial density of 120,000 to 160,000 cells/ml) of approximately 48 hours followed by and incubation of 2 hours with the MTS/PMS Reagent is optimal.

In order to establish the accuracy of this assay a Positive Control consisting of 50 µM Methotrexate should not decrease the net absorbance to less than 90% of the Negative Control (CCL155 cells are somewhat resistant to methotrexate) is utilized.

In order to establish the accuracy of this assay a Positive Control consisting of 50 µM Methotrexate should show less than 75% of the net absorbance of the Negative Control is utilized.

ANIMAL TOXCITY BIOASSAY

Acute toxicity was studied on white mice of both sexes with weight ranging between 18–26 grams under intraperitoneal injection of 2% solution of tested compound in starch (the compound was dissolved in starch slime and injected) on the basis of 0.1 ml of solution per 10 g of the animal weight. Each dose was tested on the group of 6 animals that were observed during 14 days period. (This method was approved by the Pharmacology committee of Russian Ministry of Health and has been widely used since 1968.) Averaged lethal dose ($LD_{50}$) of the compound was computed using results of experiments on 5–7 groups of animals using method of Litchfield and Wilkinson. (Belenkii M. L. "Elements of quantative determination of the pharmacological effect," Leningrad, 1963, 71 page).

USE OF THE INVENTION FOR TREATMENT OF HUMAN MYELOMA

The compounds of the invention facilitate disclosure of compounds having the property of anti-tumor activity against human myeloma including: 4-(4-Chloro-phenyl)-2-(N'-fluoren-9-ylidene-hydrazino)-4-oxo-but-2-enoic acid methyl ester (OF-07); 2-{N'-[(2-Bromo-phenyl)-phenyl-methylene]-hydrazino}-4-oxo-4-phenyl-but-2-enoic acid methyl ester (OF-09); 2-{N'-[(4-Dimethylamino-phenyl)-phenyl-methylene]-hydrazino}-4-oxo-4-phenyl-but-2-enoic acid methyl ester (OF-10) and 2-{N'-[1-(4-Chloro-phenyl)-ethylidene]-hydrazino}-4-oxo-4-phenyl-but-2-enoic acid methyl ester (OF-20); 2-(N'-Fluoren-9-ylidene-hydrazino)-5,5-dimethyl-4-oxo-hex-2-enoic acid methyl ester (OF-06); 4-(4-Ethoxy-phenyl)-2-(N'-fluoren-9-ylidene-hydrazino)-2-hydroxy-4-oxo-butyric acid methyl ester (OF-13); 4-benzoyl-3-benzoyloxy-2-(2-oxo-2H-1,4-benzoxazin-3-yl) pyrido[2,1-c][1,4]benzoxazin-1,5-dione (1F-18), 4-Chloro-4-(4-ethoxy-phenyl)-2-(fluoren-9-ylidene-hydrazono)-but-3-enoic acid methyl ester (3F-19); and 2-(N'-Fluoren-9-ylidene-hydrazino)-4-oxo-4-phenyl-but-2-enoic acid methyl ester (1F-04) which are unique in humans as therapeutic means for the eradication human myeloma can be used in a pharmaceutical composition comprising a non-toxic effective amount of the referenced compound or a tautomeric form thereof or a pharmaceutically acceptable salt thereof or pharmaceutically acceptable solvate thereof, and a pharmaceutically acceptable carrier thereof.

For administration to man in the curative or prophylactic treatment of human myeloma in vitro dosages of compounds of the invention will generally be in the range of from 5 to 500 mg daily for an average adult patient (70 kg). Thus for a typical adult patient, individual tablets or capsules contain from 2–500 mg of active compound, in a suitable pharmaceutically acceptable vehicle or carrier, for administration in single or multiple doses, once or several times per day. Dosages for intraveneous, buccal or sublingual administration will typically be within the range of from 5–1000 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

The maximum human non-toxic one time administration dose for the compound(s) of the invention appears to be from 100 to 1000 mg.

For human use, the compounds of the invention can be administered alone or jointly, but will generally be administered in admixture with a pharmaceutical carrier selected with regard to the intended route of administration and standard pharmaceutical practice. For example, they may be administered orally, buccally or sublingually, in the form of tablets containing excipients such as starch or lactose, or in capasules or ovules either alone or in admixture with excipients, or in the form of elixirs or suspensions containing flavouring or colouring agents. The compounds may also be injected parenterally, for example intraveneously, intramuscularly, subcutaneously or intracoronarily. For parenteral administration, they are best used in the form of a sterile aqueous solution which may contain other substances, for example enough salts or glucose to make the solution isotonic with blood.

The invention thus provides a method for the treatment of myeloma in a human mammal which comprises administering an effective, non-toxic, amount of a compound according to the invention or a tautomeric form thereof and/or a pharmaceutically acceptable salt thereof and/or a pharmaceutically acceptable solvate thereof, to a myeloma invaded human mammal in need thereof.

ADVANTAGES OF THE INVENTION

Melphalan/Prednisone combination still remains the first line treatment for myeloma. There is no survival advantage when MP (Melphalan-Prednisone) is compared with other various intravenous combination chemotherapeutic agents, e.g. VAD (Vincristine, Adriamycin, Decadron). Toxicity for Melphalan: LD50 in mice 23 mg/kg, it should be compared with the toxicity in the range 1000–1500 mg/kg for the claimed compounds. Claimed compounds have toxicity at least 50 times lower.

The oral Melphalan-Prednisone regime has an associated risk of secondary leukemia and care must be taken and potential side effects explained to the patients (especially in the younger age group).

Claimed compounds create a basis for further development of the anti-myeloma drugs with lower toxicity and less side effects.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A derivative of a 4-oxo-2-butenoic acid having the property of anti-myeloma activity, wherein said derivative is selected from the group consisting of:

4-(4-Chloro-phenyl)-2-(N'-fluoren-9-ylidene-hydrazino)-4-oxo-but-2-enoic acid methyl ester:

2-{N'-[(2-Bromo-phenyl)-phenyl-methylene]-hydrazino}-4-oxo-4-phenyl-but-enoic acid methyl ester;

2-{N'-[(4-Dimethylamino-phenyl)-phenyl-methylene]-hydrazino}-4-oxo-4-phenyl-but-2-enoic acid methyl ester; and -2-{N'-[1-(4-Chloro-phenyl)-ethylidene]-hydrazino}-4-oxo-4-phenyl-but-2-enoic acid methyl ester.

2. A method of treating myeloma in a human being in need of such treatment, comprising administering to said human being one or more derivatives of 4-oxo-2-butenoic acid according to claim 1.

* * * * *